US00PP24019P2

(12) United States Plant Patent
Smith

(10) Patent No.: US PP24,019 P2
(45) Date of Patent: Nov. 5, 2013

(54) ***CHRYSANTHEMUM* PLANT NAMED 'CIFZ0020'**

(50) Latin Name: *Chrysanthemum×morifolium*
Varietal Denomination: CIFZ0020

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 119 days.

(21) Appl. No.: 13/374,630

(22) Filed: Jan. 4, 2012

(51) Int. Cl.
*A01H 5/00* (2006.01)

(52) U.S. Cl.
USPC ..... Plt./290

(58) Field of Classification Search
USPC ..... Plt./290, 287, 293
See application file for complete search history.

*Primary Examiner* — Howard Locker
(74) *Attorney, Agent, or Firm* — Joshua L. Price

(57) ABSTRACT

A new *Chrysanthemum* plant named 'CIFZ0020' particularly distinguished by the small orange-red inflorescences, strong peduncles, medium green foliage, with compact and mounded plant habit.

1 Drawing Sheet

Latin name of the genus and species of the plant claimed: *Chrysanthemum×morifolium.*

Varietal denomination: 'CIFZ0020'.

BACKGROUND OF THE NEW PLANT

The present invention comprises a new *Chrysanthemum*, botanically known as *Chrysanthemum×morifolium*, and hereinafter referred to by the variety name 'CIFZ0020'.

'CIFZ0020' is a product of a planned breeding program. The new cultivar has small orange-red inflorescences, strong peduncles, medium green foliage, with compact and mounded plant habit.

'CIFZ0020' originates as a natural whole plant mutation of 'CIFZ0021', U.S. Ser. No. 13/385,260, filed Feb. 10, 2012. 'CIFZ0020' was discovered and selected by the inventor as a single flowering plant within a population of the parent cultivar in a controlled breeding program in Alva, Fla. in November 2009. The parent cultivar 'CIFZ0021' has dark pink inflorescences and a slightly faster blackcloth flowering response time.

The first act of asexual reproduction of 'CIFZ0020' was accomplished when vegetative cuttings were propagated from the initial selection in January 2010 in a controlled environment in Alva, Fla., USA.

BRIEF SUMMARY OF INVENTION

Horticultural examination of plants grown from cuttings of the plant initiated in January 2010, and continuing thereafter, has demonstrated that the combination of characteristics as herein disclosed for 'CIFZ0020' are firmly fixed and are retained through successive generations of asexual reproduction.

'CIFZ0020' has not been observed under all possible environmental conditions. The phenotype may vary significantly with variations in environment such as temperature, light intensity, and day length.

Plant Breeder's Rights for this cultivar were applied for in Canada on Feb. 24, 2011, #11-7182, in CPVO on Mar. 30, 2011, #2011/0793, and in the Republic of Korea on Jan. 31, 2012, #2012-78. 'CIFZ0020' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0020' with colors being as true as possible with an illustration of this type.

The photographic drawing shows a flowering plant of the new variety, and a close-up of the flowers.

DETAILED BOTANICAL DESCRIPTION

The plant descriptions, measurements and aforementioned photographs were taken outdoors in Gilroy, Calif. in early August 2011. The plants were growing in an outdoor potted plant trial, in one gallon pots, in full sun. These plants were approximately 9-10 weeks of age. These plants were not pinched.

Color references are made to The Royal Horticultural Society Colour Chart (R.H.S.) 2001.

TABLE 1

DIFFERENCES BETWEEN THE NEW VARIETY 'CIFZ0020' AND A SIMILAR VARIETY

| | 'CIFZ0020' | 'Delightful Yovictoria' (U.S. Plant Pat. No. 17,450) |
|---|---|---|
| Flower size: | Little smaller | Little larger |
| Inflorescence color: | Little darker | Little lighter |
| Overall plant size: | Little smaller | Little larger |
| Blackcloth flowering response time: | Slower | Faster |

Plant:

*Form, growth and habit.*—Herbaceous garden-type. Stems upright and outwardly spreading on short, mounded and compact plants. Freely branching with strong peduncles.

*Plant height.*—13.0-14.0 cm.

*Plant height (inflorescence included).*—17.0-18.0 cm.

*Plant width.*—32.0-35.0 cm.

Roots:

*Number of days to initiate roots.*—About 4-5 days at about 22 degrees C.

*Number of days to produce a rooted cutting.*—About 7-9 days at 22 degrees C.

*Type.*—Fine, fibrous, free branching.

*Color.*—RHS N155B but whiter.

Foliage:

*Arrangement.*—Alternate, simple.

*Immature, leaf color, upper surface.*—Closest to RHS 137A.

*Lower surface: Between RHS* 138A and RHS 138B.

*Mature, leaf color, upper surface.*—Closest to RHS 137A.

*Lower surface.*—Between RHS 138A and RHS 138B.

*Length.*—3.2-3.8 cm.

*Width.*—2.7-3.0 cm.

*Shape.*—Ovate.

*Base shape.*—Attenuate.

*Apex shape.*—Mucronulate.

*Margin.*—Irregularly and palmately lobed; serrate.

*Texture, upper surface.*—Bifid T-shaped hairs.

*Lower surface.*—Bifid T-shaped hairs.

*Color of veins, upper surface.*—RHS 144B, but indistinct upper in upper portions.

*Color of veins, lower surface.*—RHS 144B.

*Petiole color.*—RHS 144B.

*Length.*—0.7-1.2 cm.

*Diameter.*—0.2-0.25 cm.

*Texture.*—Bifid T-shaped hairs.

Stem:

*Quantity of main branches per plant.*—About 10.

*Color of stem.*—Closest to RHS 144A.

*Length of stem.*—10.0-12.0 cm.

*Diameter.*—0.5 cm.

*Length of internodes.*—0.5-1.0 cm.

*Texture.*—Bifid T-shaped hairs.

*Color of peduncle.*—Closest to RHS 144A.

*Length of peduncle.*—5.0 cm.

*Peduncle diameter.*—0.2 cm.

*Texture.*—Bifid T-shaped hairs.

Inflorescence:

*Type.*—Compositae type, solitary inflorescences (decorative-type) borne terminally above foliage, ray florets arranged acropetally.

*Quantity of inflorescences per plant.*—About 30 open and over 100 buds.

*Lastingness of individual blooms on the plant.*—About 4 weeks.

*Fragrance.*—Slightly spicy.

Bud (just before opening/showing color):

*Color.*—Between RHS 185A and RHS 185B.

*Length.*—1.0-1.3 cm.

*Width.*—1.0-1.5 cm.

*Shape.*—Oblate.

Immature inflorescence:

*Diameter.*—2.5-2.7 cm.

*Color of ray florets, upper surface.*—RHS 4B basally with RHS N34A towards the apex.

*Lower surface.*—RHS 5C basally with RHS N34C towards the apex.

Mature inflorescence:

*Diameter.*—4.0-4.5 cm.

*Depth.*—1.3-1.5 cm.

*Total diameter of 'disc'.*—0.3-0.4 cm.

*Receptacle height.*—0.3-0.4 cm.

*Receptacle diameter.*—0.4-0.5 cm.

Ray florets:

*Average quantity of florets.*—About 150 in several whorls.

*Color of florets, upper surface.*—RHS 4B overlaid with shades of RHS 22B and overlaid heavier with RHS 179A to RHS 179B, more so at the apex and margins.

*Lower surface.*—RHS 12C basally, overlaid RHS 176C, especially at the center of the petal, and with RHS 176A at the apex.

*Length.*—1.4-1.8 cm.

*Width.*—0.6-0.75 cm.

*Shape.*—Widely obovate.

*Apex shape.*—Irregularly praemorse.

*Margin.*—Entire.

*Texture, upper surface.*—Papillose.

*Lower surface.*—Papillose.

Disc florets:

*Average quantity of florets.*—6.

*Color of florets.*—RHS 1C with RHS 13A to RHS 13B upper with marks of RHS N34C.

*Length.*—0.3 cm.

*Width.*—0.1 cm.

*Shape.*—Tubular, elongated.

*Apex shape.*—Acute, 5 pointed.

Phyllaries:

*Quantity.*—About 20.

*Color, upper surface.*—RHS 138A but slightly darker.

*Lower surface.*—RHS 138B.

*Length.*—0.4 cm.

*Width.*—0.15-0.2 cm.

*Shape.*—Lanceolate.

*Apex shape.*—Acute.

*Base.*—Fused.

*Margins.*—Entire; some papery.

*Texture, upper surface.*—Glabrous.

*Lower surface.*—Bifid T-shaped hairs.

Reproductive organs:

*Pistil.*—1, found on both floret types.

*Length.*—0.4-0.45 cm.

*Style color.*—Closest to RHS 1B.

*Style length.*—0.3 cm.

*Stigma color.*—RHS 3A.

*Stigma shape.*—Bi-parted.

*Ovary color.*—RHS 155C.

*Ovary width.*—0.05 cm.

*Ovary length.*—0.1 cm.

*Stamens.*—4, found on only disc florets.

*Color of filaments.*—RHS 1C.

*Length filaments.*—0.2 cm.

*Anther color.*—RHS 15A.

*Anther length.*—0.2 cm.

*Anther shape.*—Oblong.

*Color of pollen.*—*N/A.*

*Pollen amount.*—None.

*Fertility/seed set.*—Has not been determined to date on this hybrid.

*Disease/pest resistance.*—Has not been determined to date on this hybrid.

What is claimed is:

1. A new and distinct variety of *Chrysanthemum* plant named 'CIFZ0020' substantially as illustrated and described herein.

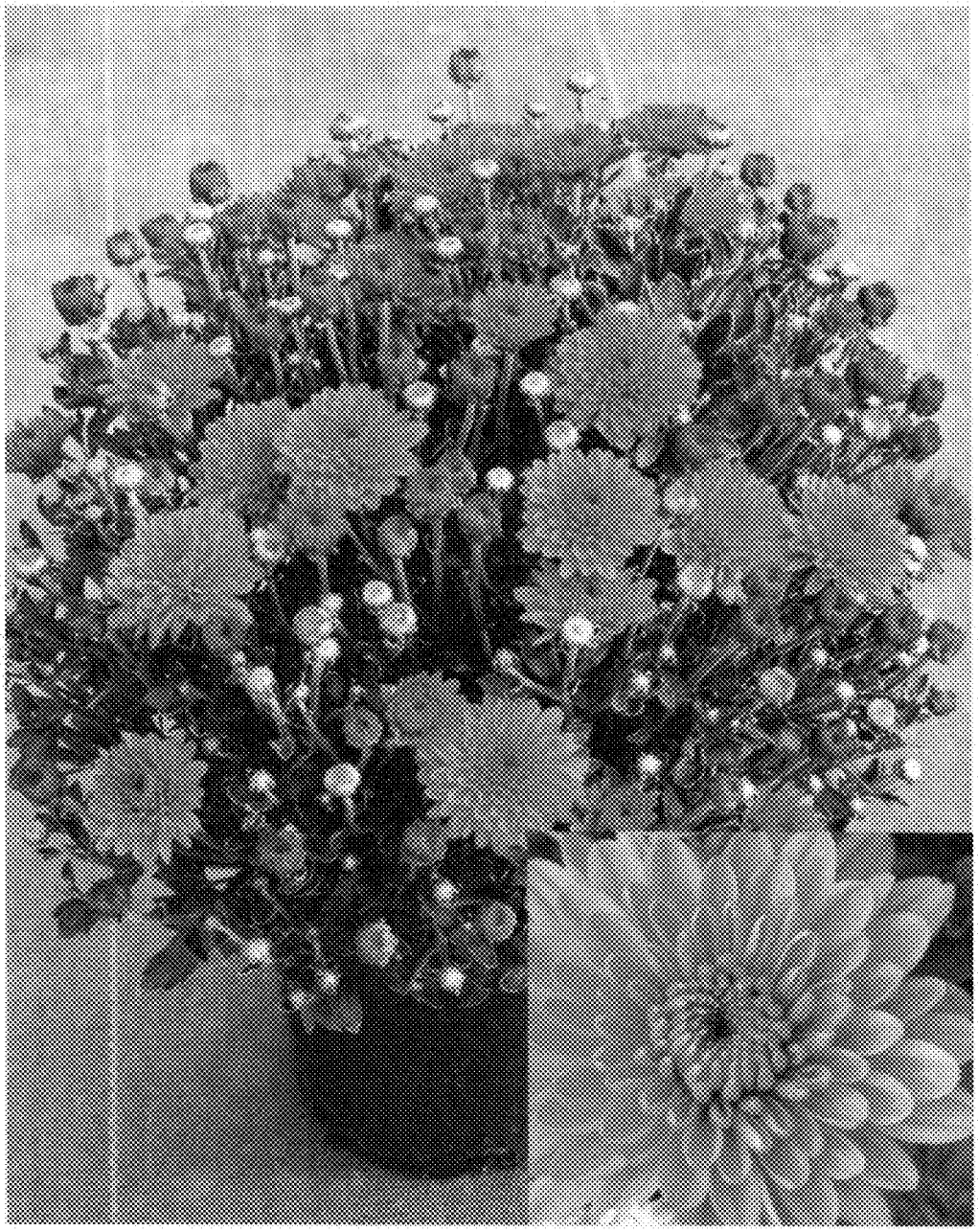

* * * * *